(12) United States Patent
Machamer et al.

(10) Patent No.: US 12,064,150 B2
(45) Date of Patent: Aug. 20, 2024

(54) SYSTEM AND METHOD FOR TREATING BONE FRACTURES

(71) Applicant: GLOBUS MEDICAL, INC., Audubon, PA (US)

(72) Inventors: David Machamer, Glen Mills, PA (US); Jonan Philip, Phoenixville, PA (US)

(73) Assignee: Globus Medical Inc., Audubon, PA (US)

( * ) Notice: Subject to any disclaimer, the term of this patent is extended or adjusted under 35 U.S.C. 154(b) by 185 days.

(21) Appl. No.: 17/578,745

(22) Filed: Jan. 19, 2022

(65) Prior Publication Data
US 2023/0225773 A1 Jul. 20, 2023

(51) Int. Cl.
*A61B 17/74* (2006.01)
*A61B 17/80* (2006.01)
*A61B 17/84* (2006.01)

(52) U.S. Cl.
CPC ......... *A61B 17/744* (2013.01); *A61B 17/746* (2013.01); *A61B 17/8061* (2013.01); *A61B 17/84* (2013.01)

(58) Field of Classification Search
CPC ..... A61B 17/744; A61B 17/84; A61B 17/746; A61B 17/8061
USPC ...................................... 606/62–68
See application file for complete search history.

(56) References Cited

U.S. PATENT DOCUMENTS

| | | | |
|---|---|---|---|
| 1,105,105 A | 7/1914 | Sherman | |
| 2,486,303 A | 10/1949 | Longfellow | |
| 3,463,148 A | 8/1969 | Treace | |
| 3,695,259 A | 10/1972 | Yost | |
| 3,716,050 A | 2/1973 | Johnston | |
| 4,219,015 A | 8/1980 | Steinemann | |
| 4,493,317 A | 1/1985 | Klaue | |
| 4,524,765 A | 6/1985 | de Zbikowski | |
| 4,651,724 A | 3/1987 | Berentey et al. | |
| 4,683,878 A | 8/1987 | Carter | |
| 4,781,183 A | 11/1988 | Casey et al. | |
| 4,867,144 A | 9/1989 | Karas et al. | |

(Continued)

FOREIGN PATENT DOCUMENTS

| CN | 201987653 U | 9/2011 |
|---|---|---|
| CN | 202313691 U | 7/2012 |

(Continued)

*Primary Examiner* — Eduardo C Robert
*Assistant Examiner* — Tara Rose E Carter

(57) ABSTRACT

An intramedullary nail includes one or more nail openings extending therethrough. The intramedullary nail is implantable within a medullary canal of the bone. A bone plate is configured to engage an outer surface of the bone. The bone plate includes one or more plate openings extending therethrough. The plate openings are spaced about the bone plate such that the bone plate is positionable to axially align the plate openings with the nail openings when the intramedullary nail is implanted within the medullary canal of the bone. An aiming guide includes one or more targeting openings. The targeting openings are spaced about the aiming guide such that the aiming guide is positionable to axially align the targeting openings with the plate openings and the nail openings for extending one or more stabilizing fasteners therethrough when the intramedullary nail is implanted within the medullary canal of the bone.

15 Claims, 18 Drawing Sheets

(56) References Cited

U.S. PATENT DOCUMENTS

| | | |
|---|---|---|
| 4,923,471 A | 5/1990 | Morgan |
| 4,966,599 A | 10/1990 | Pollock |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,468,242 A | 11/1995 | Reisberg |
| D365,634 S | 12/1995 | Morgan |
| 5,489,305 A | 2/1996 | Morgan |
| 5,527,311 A | 6/1996 | Procter et al. |
| 5,578,036 A | 11/1996 | Stone et al. |
| 5,601,553 A | 2/1997 | Trebing et al. |
| 5,676,667 A | 10/1997 | Hausman |
| 5,690,631 A | 11/1997 | Duncan et al. |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,746,742 A | 5/1998 | Runciman et al. |
| 5,766,175 A | 6/1998 | Martinotti |
| 5,766,176 A | 6/1998 | Duncan |
| 5,779,706 A | 7/1998 | Tschakaloff |
| 5,785,712 A | 7/1998 | Runciman et al. |
| 5,797,914 A | 8/1998 | Leibinger |
| 5,814,048 A | 9/1998 | Morgan |
| 5,925,048 A | 7/1999 | Ahmad et al. |
| 5,938,664 A | 8/1999 | Winquist et al. |
| 5,961,519 A | 10/1999 | Bruce et al. |
| 5,980,540 A | 11/1999 | Bruce |
| 6,001,099 A | 12/1999 | Huebner |
| 6,071,291 A | 6/2000 | Forst et al. |
| 6,093,201 A | 7/2000 | Cooper et al. |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| D458,683 S | 6/2002 | Bryant et al. |
| D458,684 S | 6/2002 | Bryant et al. |
| 6,533,786 B1 | 3/2003 | Needham et al. |
| D479,331 S | 9/2003 | Pike et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,090,676 B2 | 8/2006 | Huebner et al. |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,341,589 B2 | 3/2008 | Weaver et al. |
| 7,344,538 B2 | 3/2008 | Myerson et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,655,047 B2 | 2/2010 | Swords |
| 7,695,472 B2 | 4/2010 | Young |
| 7,717,946 B2 | 5/2010 | Oepen et al. |
| 7,722,653 B2 | 5/2010 | Young et al. |
| 7,740,648 B2 | 6/2010 | Young et al. |
| D622,853 S | 8/2010 | Raven, III |
| 7,771,457 B2 | 8/2010 | Kay et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,118,848 B2 | 2/2012 | Ducharme et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,384 B2 | 8/2013 | Beutter et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,540,755 B2 | 9/2013 | Whitmore |
| 8,551,095 B2 | 10/2013 | Fritzinger et al. |
| 8,551,143 B2 | 10/2013 | Norris et al. |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |

(56) References Cited

U.S. PATENT DOCUMENTS

| | | |
|---|---|---|
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 | 10/2015 | Fritzinger et al. |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |
| 9,180,020 B2 | 11/2015 | Gause et al. |
| 9,211,151 B2 | 12/2015 | Weaver et al. |
| 9,259,217 B2 | 2/2016 | Fritzinger et al. |
| 9,259,255 B2 | 2/2016 | Lewis et al. |
| 9,271,769 B2 | 3/2016 | Batsch et al. |
| 9,283,010 B2 | 3/2016 | Medoff et al. |
| 9,295,506 B2 | 3/2016 | Raven, III et al. |
| 9,314,284 B2 | 4/2016 | Chan et al. |
| 9,320,554 B2 | 4/2016 | Greenberg et al. |
| 9,322,562 B2 | 4/2016 | Takayama et al. |
| 9,370,388 B2 | 6/2016 | Globerman et al. |
| D765,851 S | 9/2016 | Early et al. |
| 9,433,407 B2 | 9/2016 | Fritzinger et al. |
| 9,433,452 B2 | 9/2016 | Weiner et al. |
| 9,468,479 B2 | 10/2016 | Marotta et al. |
| 9,480,512 B2 | 11/2016 | Orbay |
| 9,486,262 B2 | 11/2016 | Andermahr et al. |
| 9,492,213 B2 | 11/2016 | Orbay |
| 9,510,878 B2 | 12/2016 | Nanavati et al. |
| 9,510,880 B2 | 12/2016 | Terrill et al. |
| 9,526,543 B2 | 12/2016 | Castaneda et al. |
| 9,545,277 B2 | 1/2017 | Wolf et al. |
| 9,549,819 B1 | 1/2017 | Bravo et al. |
| 9,566,097 B2 | 2/2017 | Fierlbeck et al. |
| 9,579,133 B2 | 2/2017 | Guthlein |
| 9,622,799 B2 | 4/2017 | Orbay et al. |
| 9,636,157 B2 | 5/2017 | Medoff |
| 9,649,141 B2 | 5/2017 | Raven, III et al. |
| 9,668,794 B2 | 6/2017 | Kuster et al. |
| 9,801,670 B2 | 10/2017 | Hashmi et al. |
| 9,814,504 B2 | 11/2017 | Ducharme et al. |
| 10,123,709 B2 | 11/2018 | Imai |
| 10,507,048 B2 | 12/2019 | Overes et al. |
| 2002/0045901 A1 | 4/2002 | Wagner et al. |
| 2004/0097937 A1 | 5/2004 | Pike et al. |
| 2005/0107796 A1 | 5/2005 | Gerlach et al. |
| 2005/0131413 A1 | 6/2005 | O'Driscoll et al. |
| 2005/0187551 A1 | 8/2005 | Orbay et al. |
| 2006/0149265 A1 | 7/2006 | James et al. |
| 2006/0241607 A1 | 10/2006 | Myerson et al. |
| 2007/0083213 A1 | 4/2007 | Stravo et al. |
| 2007/0173840 A1 | 7/2007 | Huebner |
| 2007/0219636 A1 | 9/2007 | Thakkar |
| 2007/0270849 A1 | 11/2007 | Orbay et al. |
| 2007/0288022 A1 | 12/2007 | Lutz |
| 2008/0021477 A1 | 1/2008 | Strnad et al. |
| 2008/0234749 A1 | 9/2008 | Forstein |
| 2008/0275510 A1 | 11/2008 | Schonhardt et al. |
| 2009/0024172 A1 | 1/2009 | Pizzicara |
| 2009/0024173 A1 | 1/2009 | Reis, Jr. |
| 2009/0118773 A1 | 5/2009 | James et al. |
| 2009/0198285 A1 | 8/2009 | Raven, III |
| 2009/0228010 A1 | 9/2009 | Gonzalez-Hernandez et al. |
| 2009/0228047 A1 | 9/2009 | Derouet et al. |
| 2009/0240252 A1* | 9/2009 | Chang ............... A61B 17/1742 |
| | | 606/96 |
| 2009/0248084 A1 | 10/2009 | Hintermann |
| 2009/0281543 A1 | 11/2009 | Orbay et al. |
| 2009/0299369 A1 | 12/2009 | Orbay et al. |
| 2009/0312760 A1 | 12/2009 | Forstein et al. |
| 2010/0057086 A1 | 3/2010 | Price et al. |
| 2010/0114097 A1 | 5/2010 | Siravo et al. |
| 2010/0121326 A1 | 5/2010 | Woll et al. |
| 2010/0274247 A1 | 10/2010 | Grady, Jr. et al. |
| 2011/0106086 A1 | 5/2011 | Laird |
| 2011/0218580 A1 | 9/2011 | Schwager et al. |
| 2012/0010667 A1 | 1/2012 | Eglseder |
| 2012/0059424 A1 | 3/2012 | Epperly et al. |
| 2012/0203227 A1 | 8/2012 | Martin |
| 2012/0209268 A1* | 8/2012 | Overes ............... A61B 17/1725 |
| | | 606/62 |
| 2012/0232599 A1 | 9/2012 | Schoenly et al. |
| 2012/0323284 A1 | 12/2012 | Baker et al. |
| 2013/0018426 A1 | 1/2013 | Tsai et al. |
| 2013/0030444 A1* | 1/2013 | Metzinger .......... A61B 17/1725 |
| | | 606/98 |
| 2013/0046347 A1 | 2/2013 | Cheng et al. |
| 2013/0060291 A1 | 3/2013 | Petersheim |
| 2013/0123841 A1 | 5/2013 | Lyon |
| 2013/0138156 A1 | 5/2013 | Derouet |
| 2013/0150902 A1 | 6/2013 | Leite |
| 2013/0165981 A1 | 6/2013 | Clasbrummet et al. |
| 2013/0211463 A1 | 8/2013 | Mizuno et al. |
| 2013/0289630 A1 | 10/2013 | Fritzinger |
| 2014/0005728 A1 | 1/2014 | Koay et al. |
| 2014/0018862 A1 | 1/2014 | Koay et al. |
| 2014/0031879 A1 | 1/2014 | Sixto, Jr. et al. |
| 2014/0066998 A1 | 3/2014 | Martin |
| 2014/0094856 A1 | 4/2014 | Sinha |
| 2014/0121710 A1 | 5/2014 | Weaver et al. |
| 2014/0180345 A1 | 6/2014 | Chan et al. |
| 2014/0277178 A1 | 9/2014 | O'Kane et al. |
| 2014/0277181 A1 | 9/2014 | Garlock |
| 2014/0316473 A1 | 10/2014 | Pfeffer et al. |
| 2014/0330320 A1 | 11/2014 | Wolter |
| 2014/0364863 A1* | 12/2014 | Prien ..................... A61B 17/17 |
| | | 606/104 |
| 2014/0378975 A1 | 12/2014 | Castaneda et al. |
| 2015/0051650 A1 | 2/2015 | Verstreken et al. |
| 2015/0051651 A1 | 2/2015 | Terrill et al. |
| 2015/0073486 A1 | 3/2015 | Marotta et al. |
| 2015/0105829 A1 | 4/2015 | Laird |
| 2015/0112355 A1 | 4/2015 | Dahners et al. |
| 2015/0134011 A1 | 5/2015 | Medoff |
| 2015/0142065 A1 | 5/2015 | Schonhardt et al. |
| 2015/0190185 A1 | 7/2015 | Koay et al. |
| 2015/0209091 A1 | 7/2015 | Sixto, Jr. et al. |
| 2015/0216571 A1 | 8/2015 | Impellizzeri |
| 2015/0223852 A1 | 8/2015 | Lietz et al. |
| 2015/0272638 A1 | 10/2015 | Langford |
| 2015/0282851 A1 | 10/2015 | Michel |
| 2015/0313653 A1 | 11/2015 | Ponce et al. |
| 2015/0313654 A1 | 11/2015 | Horan et al. |
| 2015/0327898 A1 | 11/2015 | Martin |
| 2015/0351816 A1 | 12/2015 | Lewis et al. |
| 2015/0374421 A1 | 12/2015 | Rocci et al. |
| 2016/0022336 A1 | 1/2016 | Bateman |
| 2016/0030035 A1 | 2/2016 | Zajac et al. |
| 2016/0045237 A1 | 2/2016 | Cerynik et al. |
| 2016/0045238 A1 | 2/2016 | Bohay et al. |
| 2016/0074081 A1 | 3/2016 | Weaver et al. |
| 2016/0166297 A1 | 6/2016 | Mighell et al. |

(56) References Cited

U.S. PATENT DOCUMENTS

| | | |
|---|---|---|
| 2016/0166298 A1 | 6/2016 | Mighell et al. |
| 2016/0183990 A1 | 6/2016 | Koizumi et al. |
| 2016/0262814 A1 | 9/2016 | Wainscott |
| 2016/0278828 A1 | 9/2016 | Ragghianti |
| 2016/0310183 A1 | 10/2016 | Shah et al. |
| 2016/0310185 A1 | 10/2016 | Sixto et al. |
| 2016/0324552 A1 | 11/2016 | Baker et al. |
| 2016/0354122 A1 | 12/2016 | Montello et al. |
| 2016/0374738 A1 | 12/2016 | Smith et al. |
| 2017/0035478 A1 | 2/2017 | Andermahr et al. |
| 2017/0042592 A1 | 2/2017 | Kim |
| 2017/0042596 A9 | 2/2017 | Mighell et al. |
| 2017/0049493 A1 | 2/2017 | Gauneau et al. |
| 2017/0065312 A1 | 3/2017 | Lauf et al. |
| 2017/0105775 A1 | 4/2017 | Ricker et al. |
| 2017/0215931 A1 | 8/2017 | Cremer et al. |
| 2018/0125545 A1 | 5/2018 | Buscaglia et al. |
| 2019/0000509 A1* | 1/2019 | Cowens ............ A61B 17/1728 |
| 2020/0069318 A1 | 3/2020 | Machamer |
| 2021/0275195 A1 | 9/2021 | Wong et al. |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| EP | 3747375 A1 | 12/2020 |
| FR | 2846870 A1 | 5/2004 |
| FR | 2928259 A1 | 9/2009 |
| JP | 2003210478 A | 7/2003 |
| JP | 2017-515554 A | 6/2017 |
| JP | 2020127742 A | 8/2020 |
| JP | 2021000440 A | 1/2021 |
| TW | 201316942 A | 5/2013 |
| WO | 2016079504 A1 | 5/2016 |

\* cited by examiner

SYSTEM AND METHOD FOR TREATING BONE FRACTURES

FIELD

The present disclosure generally relates to treating bone fractures.

BACKGROUND

Following an injury to a long bone, such as a fracture of the femur or tibia, one or more fixation devices may be used to immobilize the fracture fragments and stabilize the long bone. Intramedullary nails, for example, may be inserted into the intramedullary canal of the bone and provide the appropriate proximal and/or distal fixation. However, known intramedullary devices may suffer from a number of disadvantages. For example, they may be susceptible to implant failure and difficulty in alignment of a fixation screw with respect to the intramedullary nail.

BRIEF SUMMARY

The present disclosure enables a fixation screw to be extended at least partially through an intramedullary nail. In one aspect, a system is provided for treating a fracture in a bone. The system includes an intramedullary nail including one or more nail openings extending therethrough for receiving one or more stabilizing fasteners. The intramedullary nail is implantable within a medullary canal of the bone. A bone plate is configured to engage an outer surface of the bone. The bone plate includes one or more plate openings extending therethrough for receiving the stabilizing fasteners. The plate openings are spaced about the bone plate such that the bone plate is positionable to axially align the plate openings with the nail openings when the intramedullary nail is implanted within the medullary canal of the bone. An aiming guide includes one or more targeting openings for receiving the stabilizing fasteners. The targeting openings are spaced about the aiming guide such that the aiming guide is positionable to axially align the targeting openings with the plate openings and the nail openings for extending the stabilizing fasteners therethrough when the intramedullary nail is implanted within the medullary canal of the bone.

In another aspect, an aiming guide is provided for treating a fracture in a bone. The aiming guide includes a body and a pair of legs extending from the body. Each leg of the pair of legs includes one or more targeting openings for receiving one or more stabilizing fasteners therethrough. The targeting openings are spaced about the pair of legs such that the aiming guide is positionable to axially align the targeting openings with one or more openings of an intramedullary nail implanted within a medullary canal of the bone.

In yet another aspect, a method is provided for treating a fracture in a bone. The method includes coupling an intramedullary nail to an insertion tool. The intramedullary nail includes one or more nail openings extending therethrough for receiving one or more stabilizing fasteners. An aiming guide is coupled to the insertion tool. The aiming guide includes one or more targeting openings for receiving the stabilizing fasteners. The intramedullary nail is implanted within a medullary canal of the bone. A bone plate includes one or more plate openings extending therethrough such that the plate openings are axially aligned with the targeting openings. The stabilizing fasteners are extended through the plate openings and the nail openings using the targeting openings.

BRIEF DESCRIPTION OF THE DRAWINGS

Corresponding reference characters indicate corresponding parts throughout the drawings.

DETAILED DESCRIPTION

Figure 1:
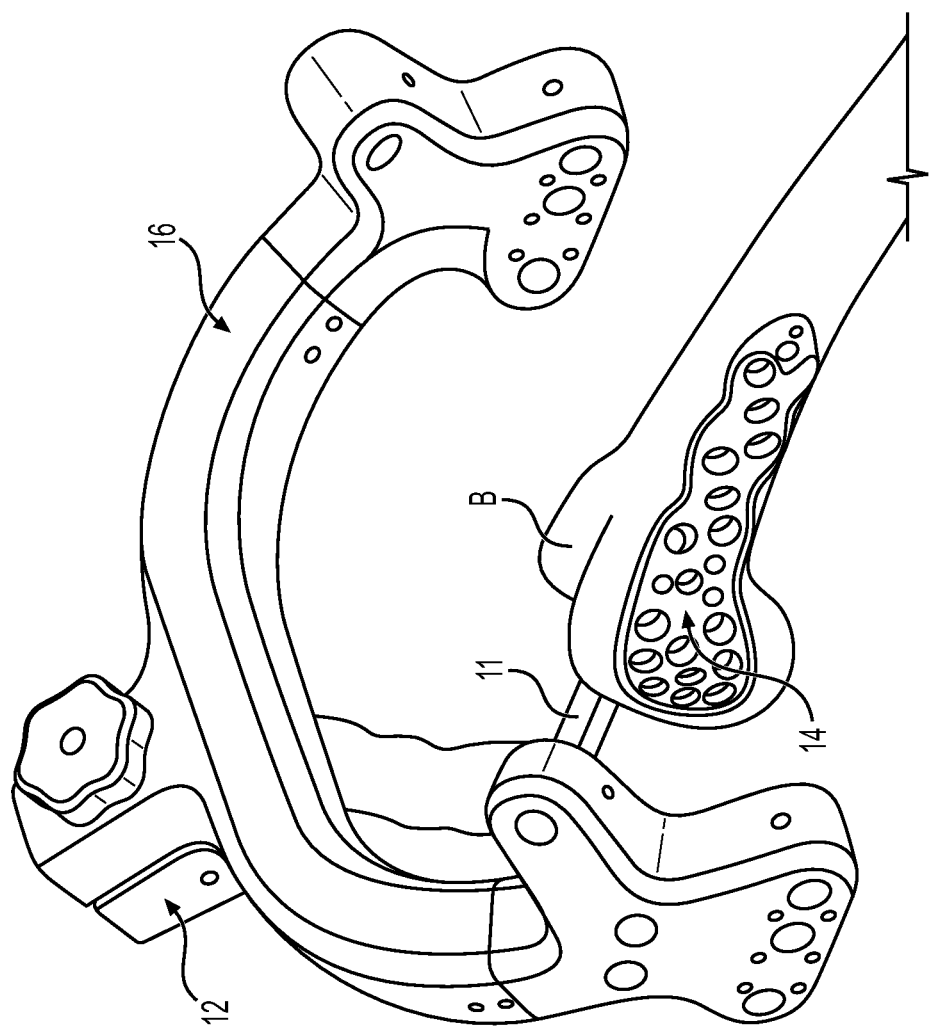
FIG. 1 is a perspective view of an example system for treating a bone fracture, including the insertion tool, an aiming guide, and a bone plate.

FIG. 1 shows a system 10 for treating a fracture in a bone B. The system 10 may include the intramedullary nail 11 and insertion tool 12, a bone plate 14 (e.g., a washer plate), and/or an aiming guide 16. Referring to FIGS. 2-6, an example insertion tool 12 may be coupled to an intramedullary nail 11 for use in handling or moving the intramedullary nail 11. The insertion tool 12 may be used, for example, to advance, retract, and/or rotate the intramedullary nail 11. In some examples, the insertion tool 12 is used to insert the intramedullary nail 11 into a long bone (e.g., after reaming).

The intramedullary nail 11 includes an elongate body extending between a distal end and a proximal end. In some examples, the intramedullary nail 11 defines a hollow channel extending axially therethrough. Alternatively, the intramedullary nail 11 may be solid along its length. The intramedullary nail 11 is configured to extend axially within the intramedullary canal of a bone. In some examples, the intramedullary nail 11 may be substantially straight. Alternatively, the intramedullary nail 11 may include one or more curves or bends that conform to the anatomical shape of the intramedullary canal.

The intramedullary nail 11 may be comprised of one or more biocompatible materials that enable the intramedullary nail to have sufficient strength to secure and hold bone. For example, the intramedullary nail 11 includes one or more of titanium, cobalt chrome, cobalt-chrome-molybdenum, stainless steel, tungsten carbide, carbon composite, polyetheretherketone (PEEK), polyethylene, ultra-high molecular weight polyethylene (UHMWPE), resorbable polylactic acid (PLA), polyglycolic acid (PGA), and/or an alloy of such materials.

Figure 2:
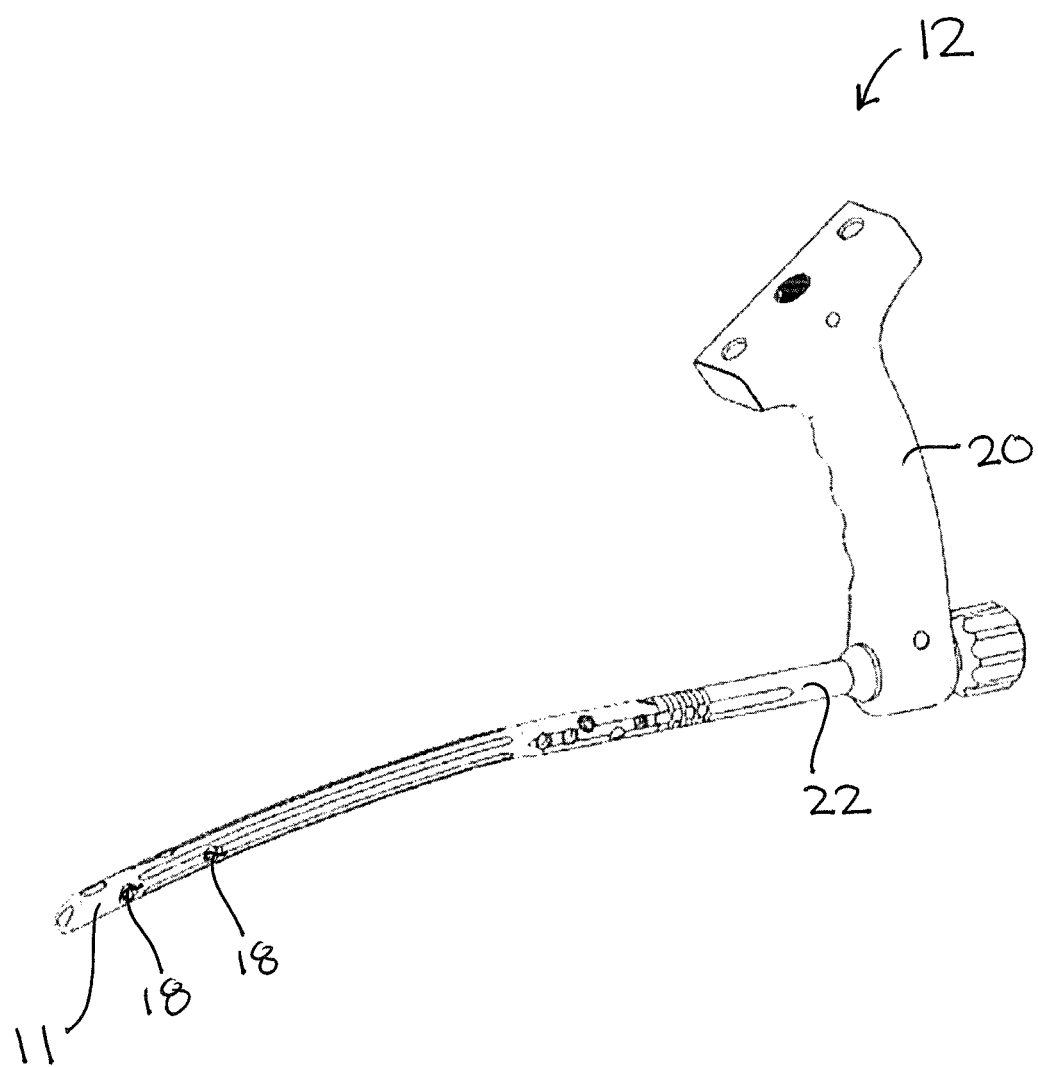
FIG. 2 is a perspective view of an example insertion tool for treating a bone fracture, including a handle and an intramedullary nail coupled to the handle.
Figure 3:
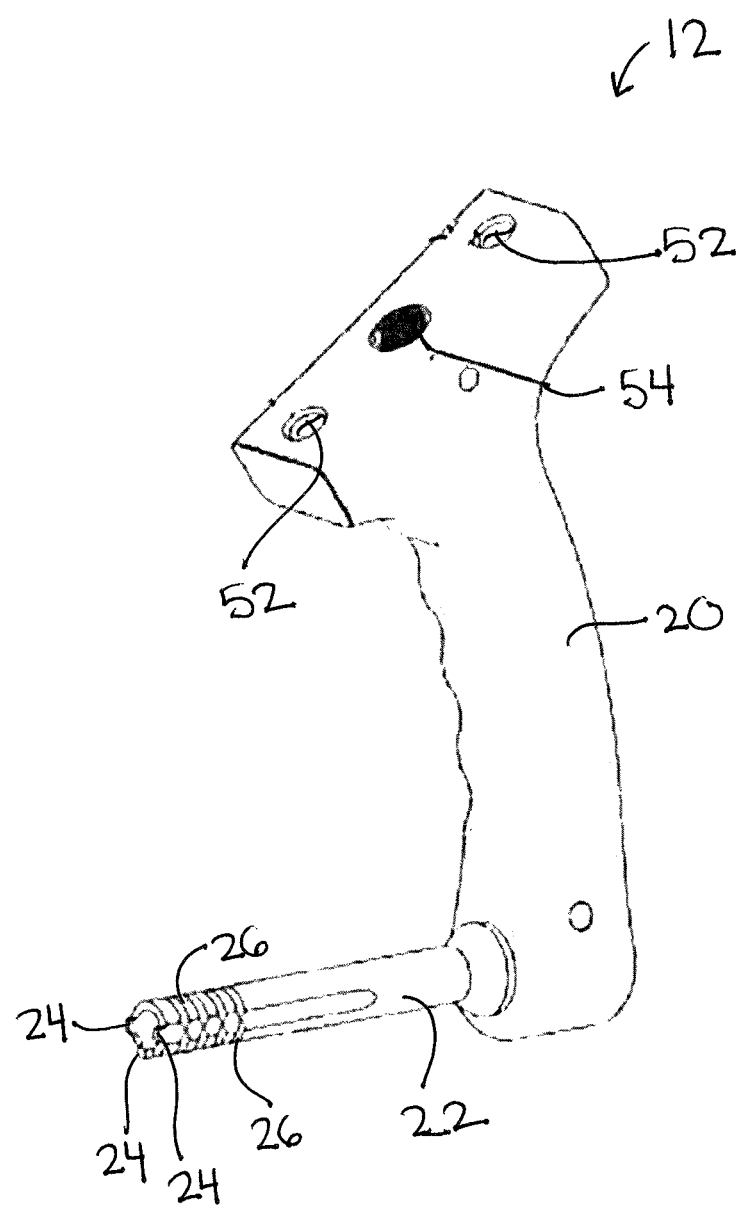
FIG. 3 is a perspective view of the insertion tool shown in FIG. 2.

As shown in FIG. 2, the intramedullary nail 11 may include one or more slots and/or nail openings 18 extending therethrough. The nail openings 18 are arranged or spaced to form an opening pattern about the intramedullary nail 11. The nail openings 18 may be configured to receive and guide one or more stabilizing fasteners (e.g., nail, screw, bolt) therethrough. In some examples, one or more nail openings 18 may include one or more threads configured to engage one or more threads of the stabilizing fasteners. Each nail opening 18 may be oriented to have a trajectory defining an angle relative to the longitudinal axis of the intramedullary nail 11. For example, the nail openings 18 may be defined to extend generally radially in the anterior-posterior (AP) and/or medio-lateral (ML) direction. Alternatively, the nail openings 18 may be oriented to have any trajectory that enables the intramedullary nail 11 to function as described herein.

The insertion tool 12 includes a handle 20 and an insertion shaft 22 extending from the handle 20 in a distal direction. The insertion shaft 22 may include one or more orientation tabs 24 that enable the intramedullary nail 11 to be desirably positioned and/or oriented relative to insertion tool 12. As shown in the current example, the insertion shaft 22 has three orientation tabs 24 distally extending from its distal end that aid in ensuring that the intramedullary nail 11 is oriented correctly when the intramedullary nail is coupled to the insertion shaft. For example, the intramedullary nail 11 may be oriented such that the nail openings 18 extend generally radially in the AP and/or ML direction. In some examples, the insertion shaft 22 may include one or more grooves 26 at a distal portion thereof to enable a user (e.g., surgeon) to locate a proximal end of the intramedullary nail 11 (e.g., under fluoroscopy). The grooves 26 may be spaced axially about 0.2 inches (about 5.0 millimeters) apart and/or extend circumferentially about an outer surface of the insertion shaft 22.

Figure 4:
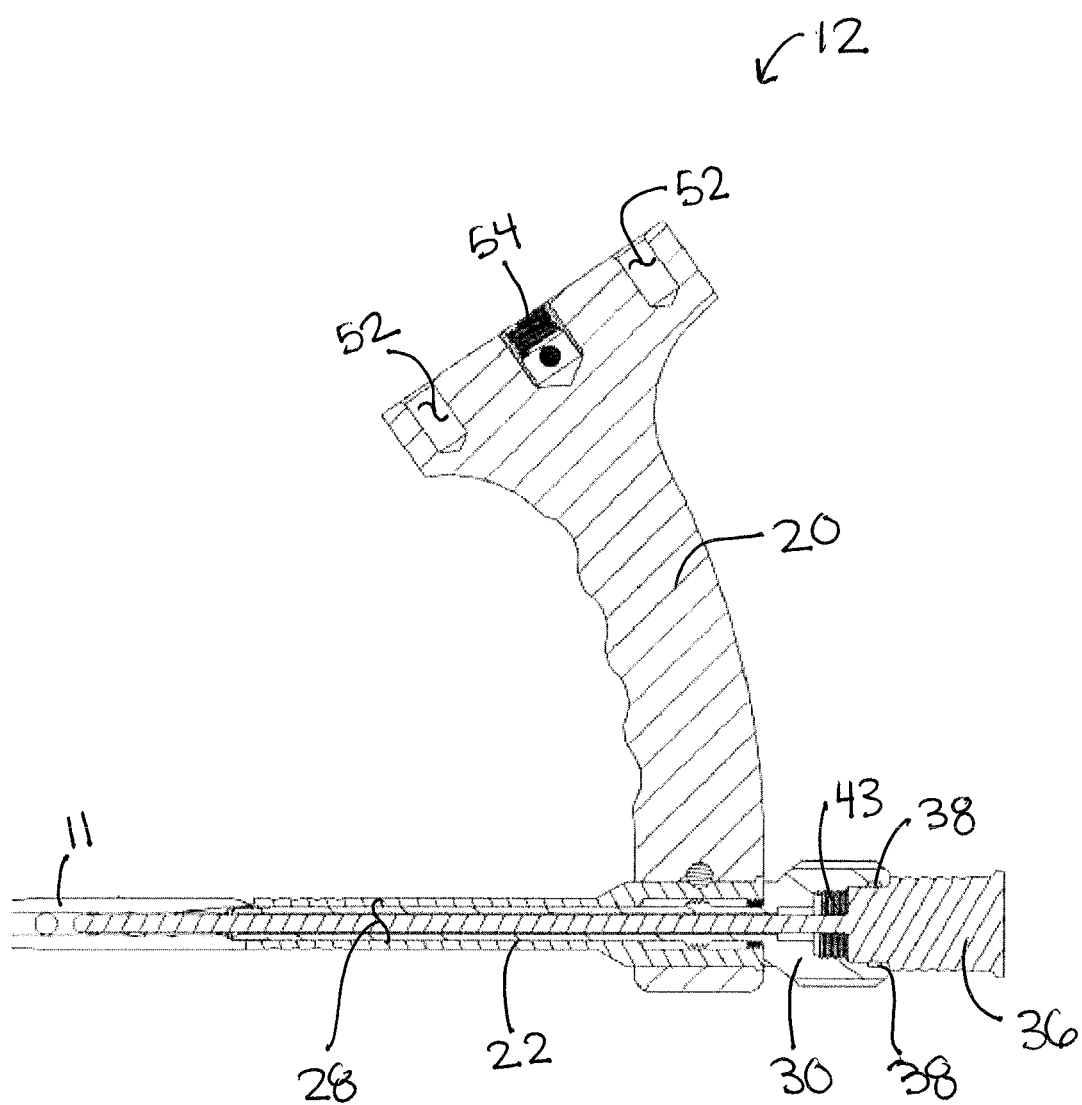
FIGS. 4 and 5 are detailed cross-sectional views of the insertion tool shown in FIG. 2 with an example assembly shaft.
Figure 5:
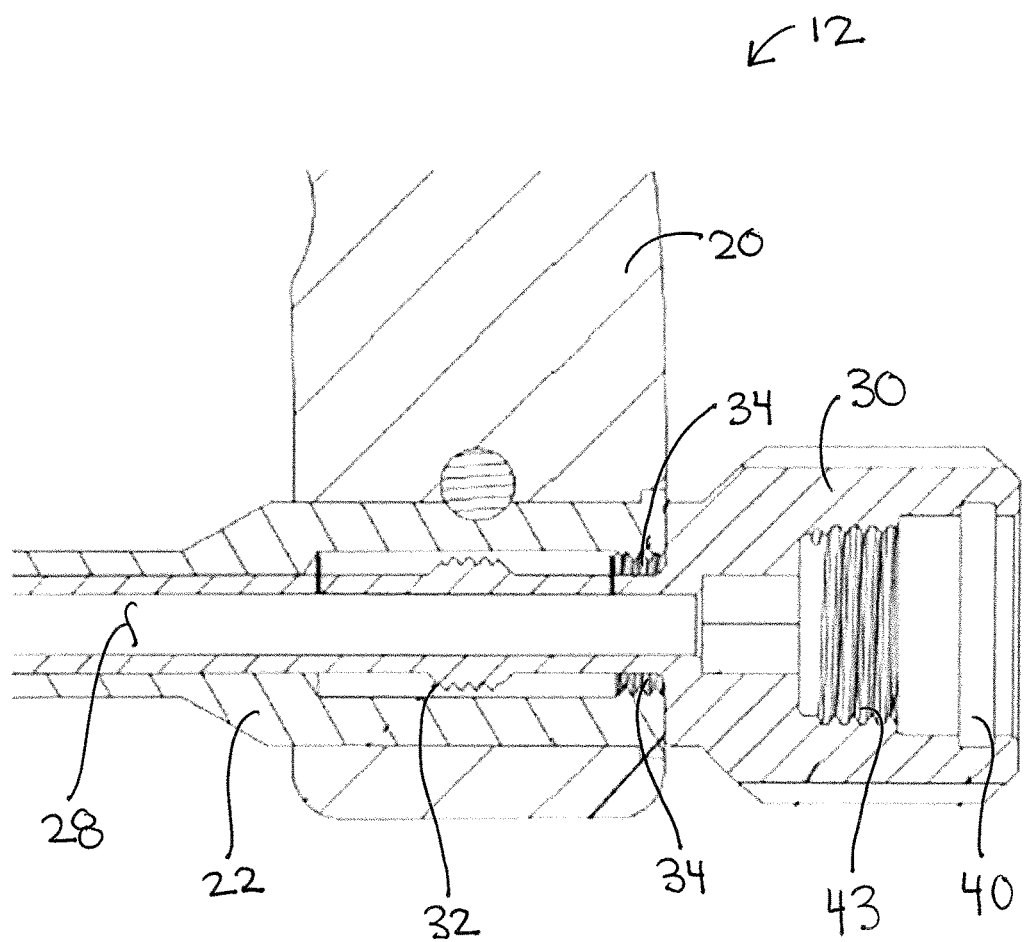

As shown in FIGS. 4 and 5, the insertion shaft 22 may extend at least partially through the handle 20 and/or include a flange at a proximal portion thereof that seats into a groove defined in a proximal surface of the handle 20. In some examples, the handle 20 is fabricated from a composite material, and/or the insertion shaft 22 is fabricated from a stainless steel material. Alternatively, the handle 20 and/or insertion shaft 22 may be fabricated from any combination of materials that enables the insertion tool 12 to function as described herein.

As shown in FIGS. 4 and 5, the insertion shaft 22 may define a cannula or channel 28 extending axially therethrough. A connection bolt 30 may be extended axially through the channel 28 of the insertion shaft 22 to facilitate quick and easy assembly of the intramedullary nail 11 onto the insertion tool 12. For example, the connection bolt 30 may be translated axially to selectively extend a distal end of the connection bolt 30 beyond a distal end of the insertion shaft 22 and into a proximal end of the intramedullary nail 11. When the connection bolt 30 is translated axially to selectively retract the distal end of the connection bolt 30, the distal end of the insertion shaft 22 acts as a stop for the intramedullary nail 11 such that the distal end of the connection bolt 30 may be withdrawn from the proximal end of the intramedullary nail 11.

The connection bolt 30 may include one or more external threads 32 configured to engage or cooperate with one or more internal threads 34 of the insertion shaft 22. As shown in FIGS. 4 and 5, when the external threads 32 of the connection bolt 30 are distal to the internal threads 34 of the insertion shaft 22 and in a cavity defined by the insertion shaft 22 (i.e., the connection bolt 30 is fully threaded into the insertion shaft 22), the threads of the connection bolt 30 and/or insertion shaft 22 are configured to prevent the external threads of the connection bolt 30 from falling out of the cavity while allowing the external threads of the connection bolt 30 to freely translate within the cavity. In this manner, the connection bolt 30 may be configured to translate axially a predetermined distance. In some examples, a user (e.g., surgeon) may strike a proximal portion of the connection bolt 30 to impact the intramedullary nail 11 through the insertion tool 12.

In some examples, an assembly shaft 36 may be used to further aid in the connection of the intramedullary nail 11 onto the insertion tool 12. As shown in FIG. 4, the assembly shaft 36 may be inserted into and through the connection bolt 30 and/or insertion shaft 22. A distal end of the assembly shaft 36 may be selectively extended beyond the distal end of insertion shaft 22 and/or connection bolt 30 and into the channel or cannula of the intramedullary nail 11. In this manner, the assembly shaft 36 may be used to align the intramedullary nail 11 with the insertion shaft 22 and/or connection bolt 30 as the intramedullary nail 11 is coupled to the insertion tool 12 (e.g., connection bolt 30). The assembly shaft 36 may include a latching feature 38 that interfaces with an undercut groove 40 in the connection bolt 30 to retain the assembly shaft 36 once inserted.

Figure 6:
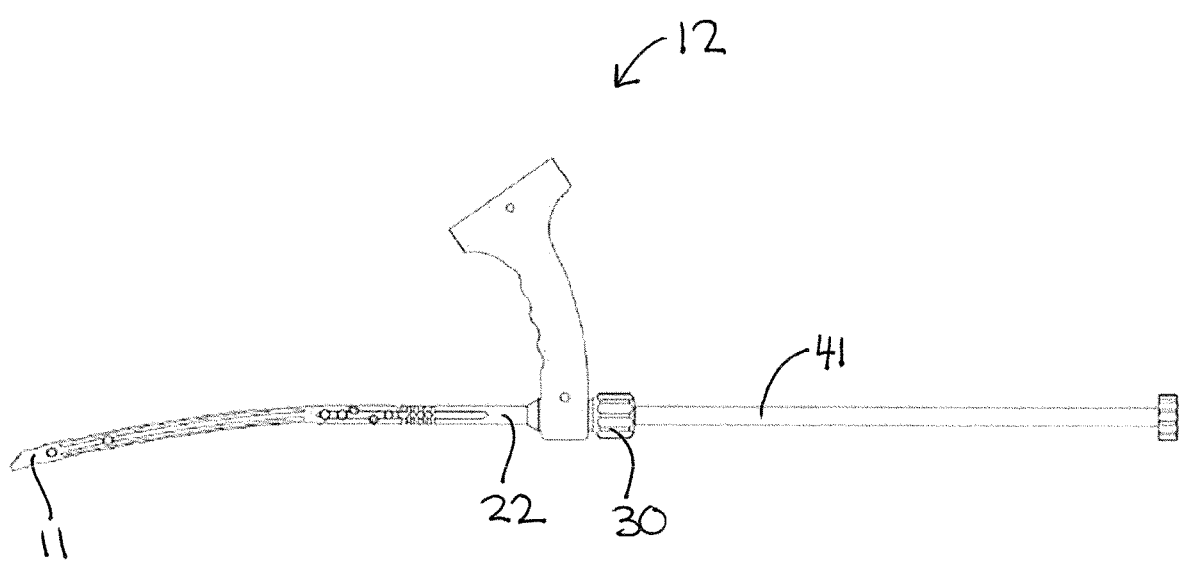
FIG. 6 is a side view of the insertion tool shown in FIG. 2 with an example backslap shaft.

As shown in FIG. 6, the insertion tool 12 may include or be coupled to a backslap shaft 41 for use in retracting the intramedullary nail 11. The backslap shaft 41 may be coupled to the insertion shaft 22 and/or connection bolt 30. For example, as shown in FIGS. 4 and 5, the connection bolt 30 may include one or more internal threads 43 for use in connecting the backslap shaft 41. In this manner, a user (e.g., surgeon) may strike a proximal portion of the backslap shaft 41 (e.g., in a proximal direction) to impact the intramedullary nail 11 through the insertion tool 12.

Figure 7:
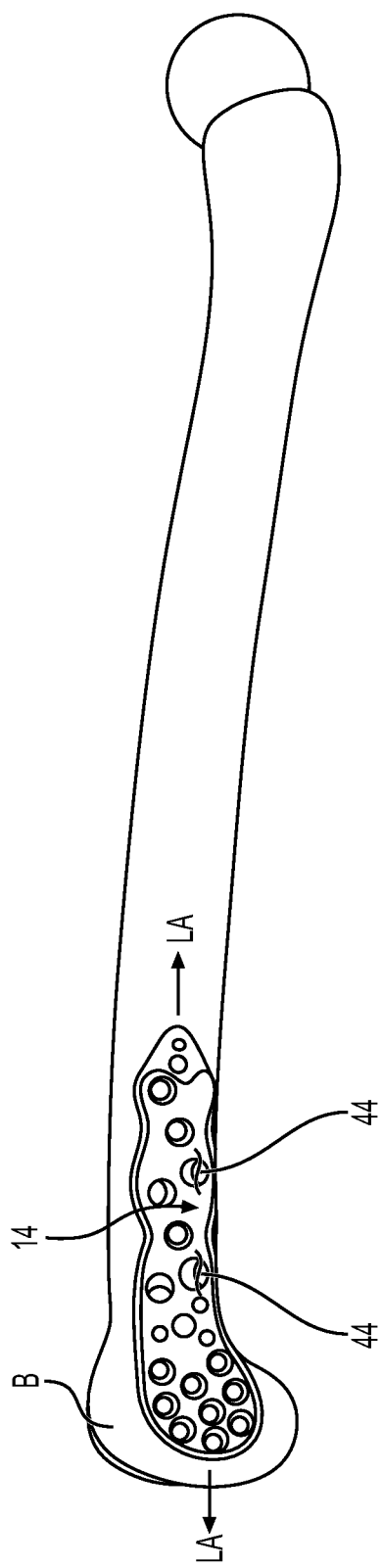
FIG. 7 is a side view of the bone plate shown in FIG. 1 coupled to a long bone.
Figure 8:
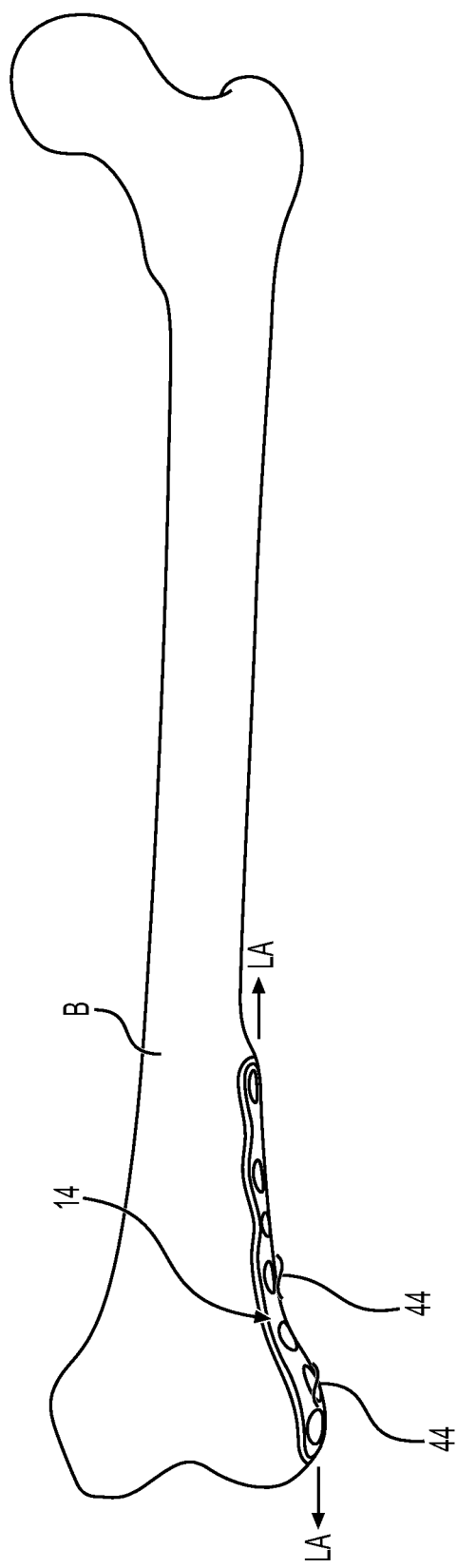
FIG. 8 is a top view of the bone plate shown in FIG. 1 coupled to the long bone.

As shown in FIGS. 7 and 8, the bone plate 14 may be oriented to extend generally along or parallel to a longitudinal axis LA of the bone B and positioned on a medial and/or lateral side of the bone B to engage at least a portion of a condyle and/or shaft of the bone B. In some examples, the bone plate 14 is configured and/or contoured to match or lie substantially parallel to a particular outer bone surface, such as an epiphysis region, a metaphysis region, and/or a diaphysis region of the bone B. In this manner, the bone plate 14 may be used to stabilize distal femur fractures as well as distal femur articular fractures as a stand-alone reduction device, a provisional fixation device, and/or a final fixation device.

In some examples, the bone plate 14 may be used with one or more stabilizing fasteners (e.g., nail, screw, bolt) to increase a load carrying capability of the construct. For example, the bone plate 14 may be used with standard locking screws and/or with dedicated washer bolts that compress the condyles of the bone B when tightened and/or provide support to the articular block and femoral shaft. In some examples, the stabilizing fasteners may be extended through one or more nail openings 18 of the intramedullary nail 11.

Figure 9:
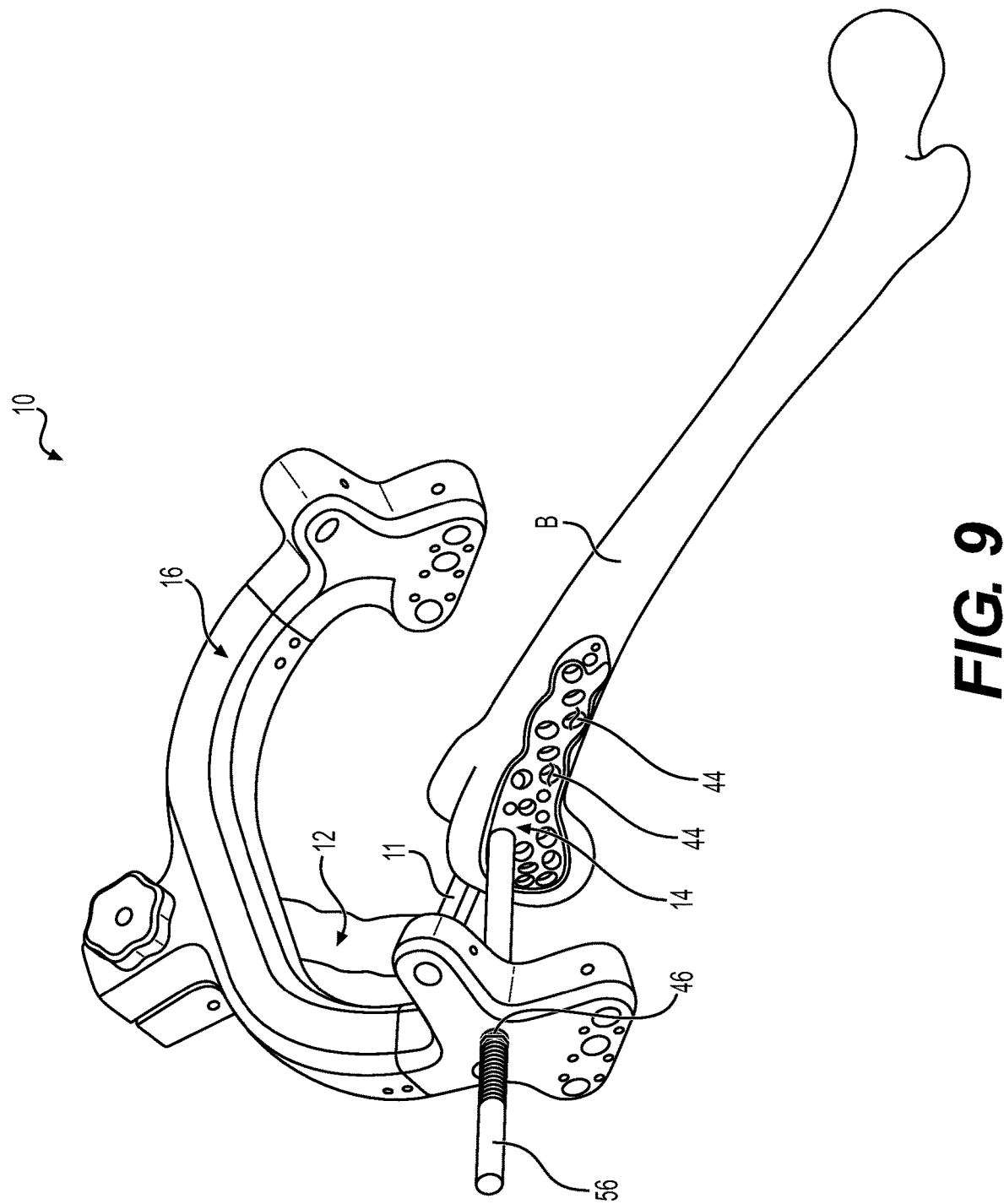
FIG. 9 is a perspective views of the system shown in FIG. 1 including driver sleeves.

As shown in FIGS. 7 and 8, the bone plate 14 may include or define one or more plate openings 44 extending therethrough that are sized, shaped, and/or configured to receive one or more stabilizing fasteners therethrough. The plate openings 44 may be arranged or spaced about the bone plate 14 to form an opening pattern that enables the stabilizing fasteners to be arranged or positioned in one or more desired stabilizing fastener patterns. The stabilizing fasteners may be extended through the plate openings 44, for example, to be in a stabilizing fastener pattern that immobilizes one or more fracture fragments, stabilizes the bone B, and/or otherwise treats a bone fracture. In some examples, as shown in FIG. 9, the bone plate 14 may be positioned and/or oriented such that the trajectory of one or more plate openings 44 substantially matches or are coaxial with one or more nail openings 18 of the intramedullary nail 11 so that the bone plate 14 and the intramedullary nail 11 may be interlocked together. The bone plate 14 may be attached with locking or non-locking screws using either freehand technique or using an aiming guide (e.g., aiming guide 16).

Figure 10:
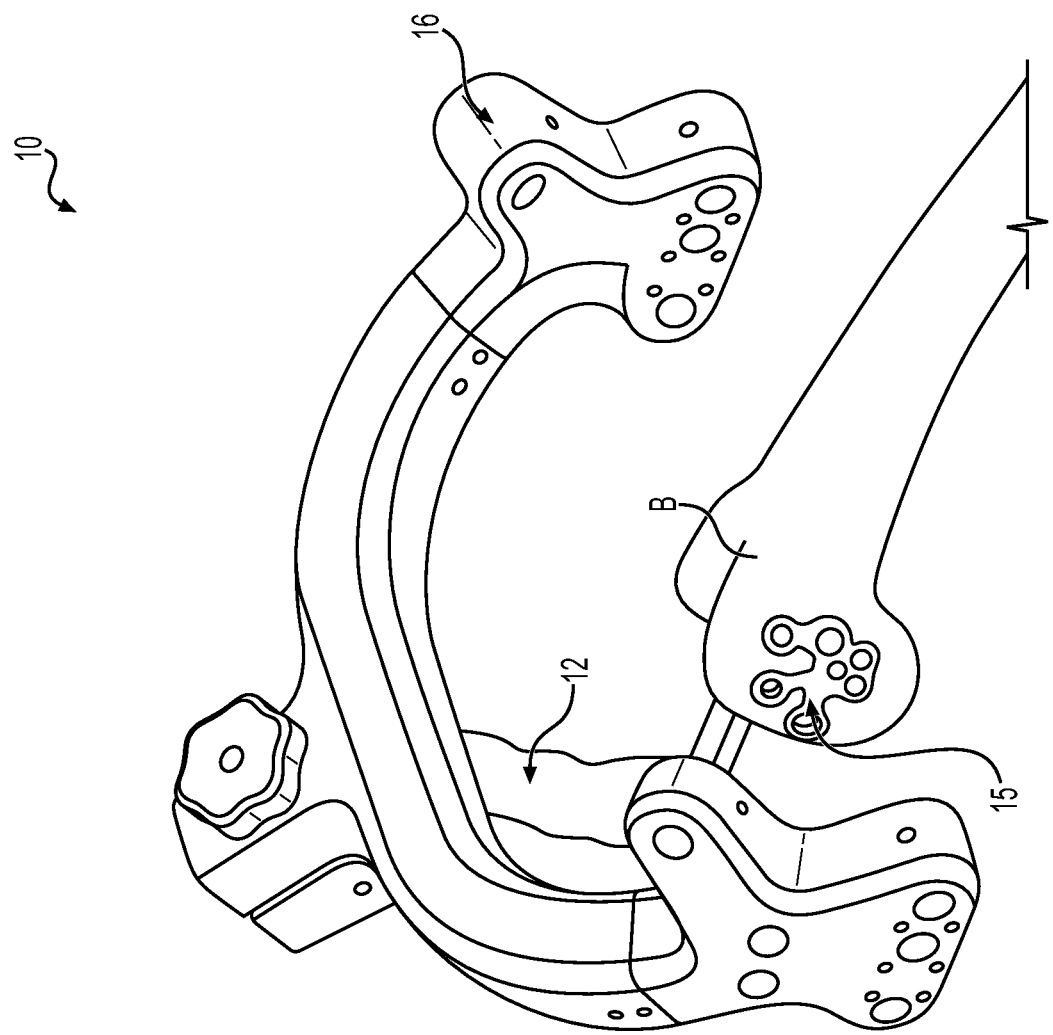
FIG. 10 is a perspective view of another example system for treating a bone fracture, including the insertion tool, the aiming guide, and another bone plate.
Figure 11:
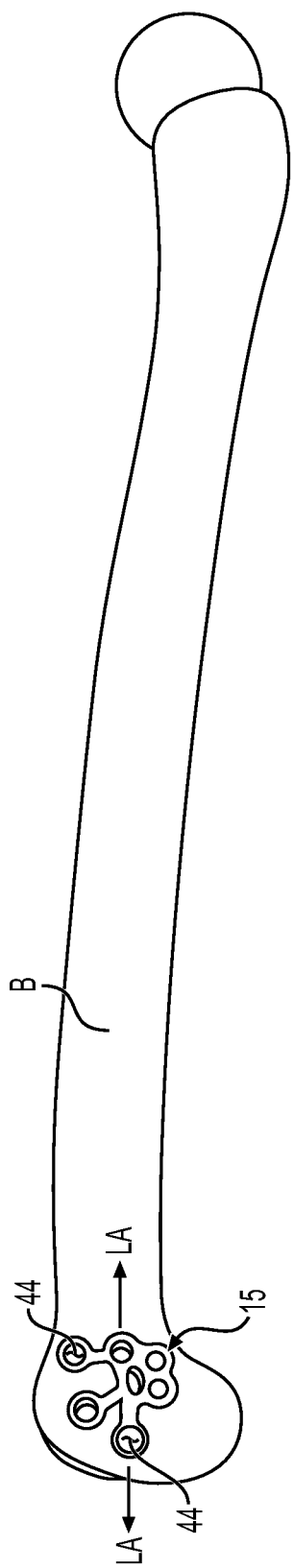
FIG. 11 is a side view of the bone plate shown in FIG. 10 coupled to a long bone.
Figure 12:
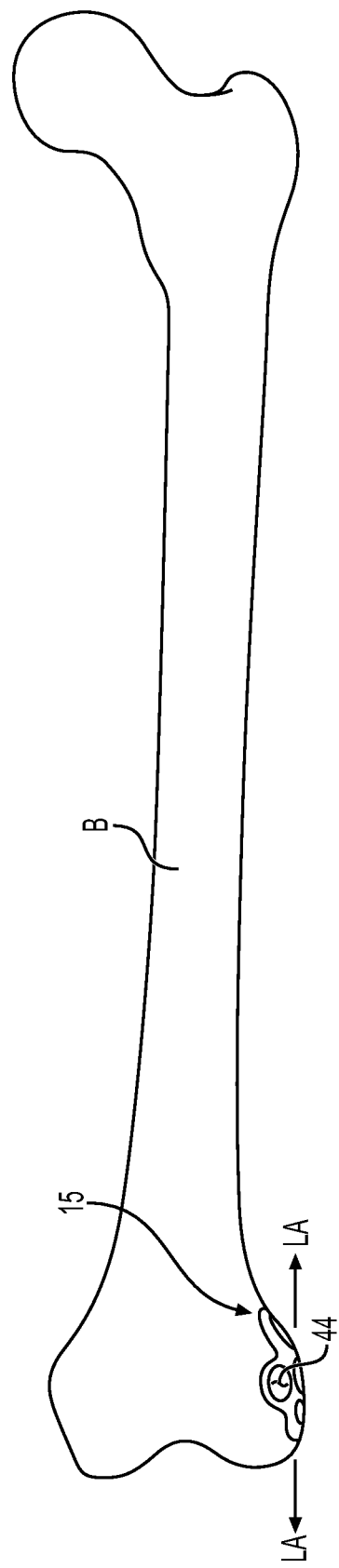
FIG. 12 is a top view of the bone plate shown in FIG. 10 coupled to the long bone.

FIGS. 10-12 show another example bone plate 15 that may be used in the system 10 for treating a fracture in the bone B. Like bone plate 14, shown in FIGS. 7-9, the bone plate 15 may be oriented to extend generally along or parallel to the longitudinal axis LA of the bone B and be positioned on a medial and/or lateral side of the bone B to engage at least a portion of a condyle and/or shaft of the bone B. While bone plate 15 has a different shape and/or configuration than that of bone plate 14, bone plate 15 may be used with one or more stabilizing fasteners, intramedullary nail 11, insertion tool 12, and aiming guide 16 in the same or a substantially similar manner.

Referring to FIGS. 1, 9, and 13-14, the aiming guide 16 may include or define one or more targeting openings 46 extending therethrough that are sized, shaped, and/or configured to receive one or more stabilizing fasteners therethrough. The aiming guide 16 is configured to enable a user (e.g., a surgeon) to target or locate one or more nail openings 18 of the intramedullary nail 11 for inserting stabilizing fasteners without fluoroscopy. For example, the targeting openings 46 may be arranged or spaced about the aiming guide 16 to form an opening pattern that enables the stabilizing fasteners to be arranged or positioned in one or more desired stabilizing fastener patterns. The stabilizing fasteners may be extended through the targeting openings 46, for example, to be in a stabilizing fastener pattern that immobilizes one or more fracture fragments, stabilizes the bone B, and/or otherwise treats a bone fracture. In some examples, one or more targeting openings 46 may be used for plate-nail targeting, washer-nail targeting, and/or blocking screw insertion. For example, blocking screws may be extended through one or more targeting openings 46 to guide the trajectory of stabilizing fasteners to gain an anatomic reduction prior to final fixation.

In some examples, the aiming guide 16 may include a body and a pair of legs extending from the body. As shown in FIGS. 1, 9, 13, and 15, the aiming guide 16 may have or include a wishbone-shaped configuration. Each leg may include one or more targeting openings 46 such that targeting openings 46 may be positioned on opposite sides of the bone B, such as medial and lateral sides. In some examples, the aiming guide 16 may be fabricated from one or more composite, radiolucent material. In this manner, the aiming guide 16 will not obstruct the view of the intramedullary nail 11 and/or bone B when using fluoroscopy due to its wishbone-shaped configuration and/or radiolucent material.

Figure 14:
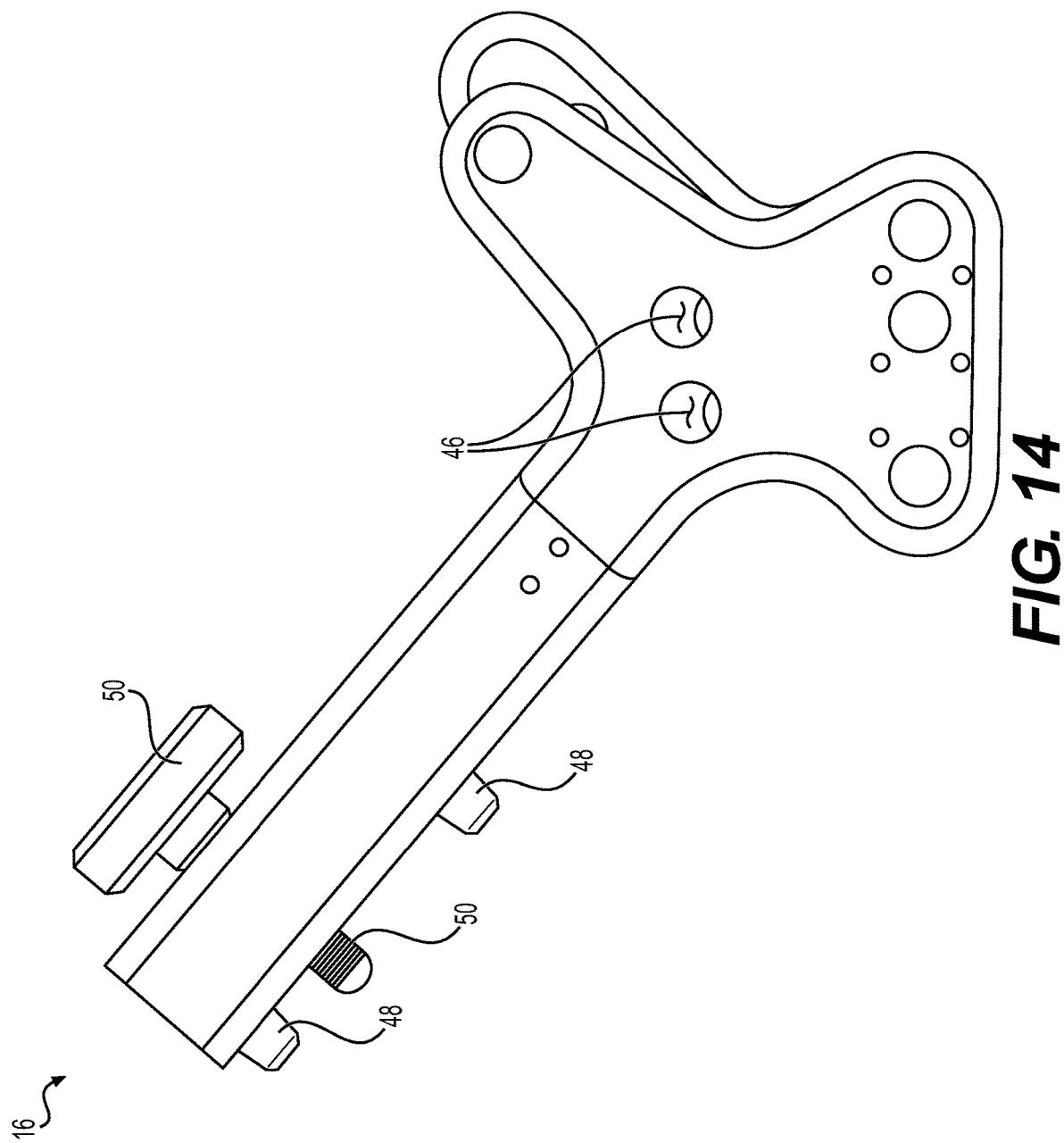
FIG. 14 is a side view of the aiming guide shown in FIG. 1.
Figure 15:
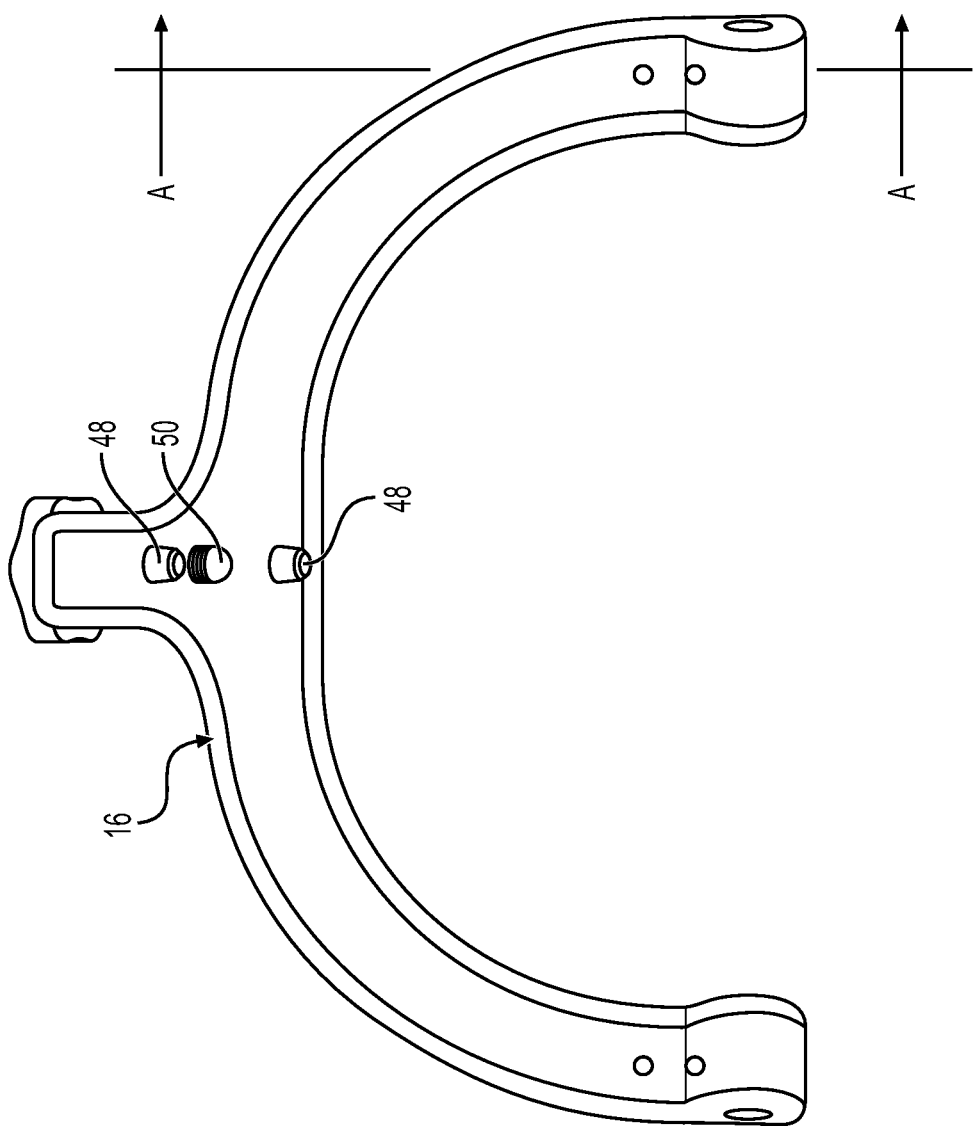
FIG. 15 is a front view of the aiming guide shown in FIG. 1.

As shown in FIGS. 14 and 15, the body of the aiming guide 16 may include one or more locating pins 48 and/or a threaded knob 50 that enables the aiming guide 16 to be desirably positioned and/or oriented relative to insertion tool 12. In some examples, the locating pins 48 are sized, shaped, and/or configured to be received in one or more locating pin openings 52 (shown in FIGS. 3 and 4) defined in an upper portion of the handle 20, and/or the threaded knob 50 is sized, shaped, and/or configured to be received in a threaded insert 54 (shown in FIGS. 3 and 4) defined in the upper portion of the handle 20. The threaded knob 50 may be used to securely couple the aiming guide 16 to the insertion tool 12. Additionally, or alternatively, the insertion tool 12 may include one or more locating pins 48 and/or the threaded knob 50, and/or the aiming guide 16 may include the one or more locating pin openings 52 and/or threaded insert 54 defined therein.

Figure 13:
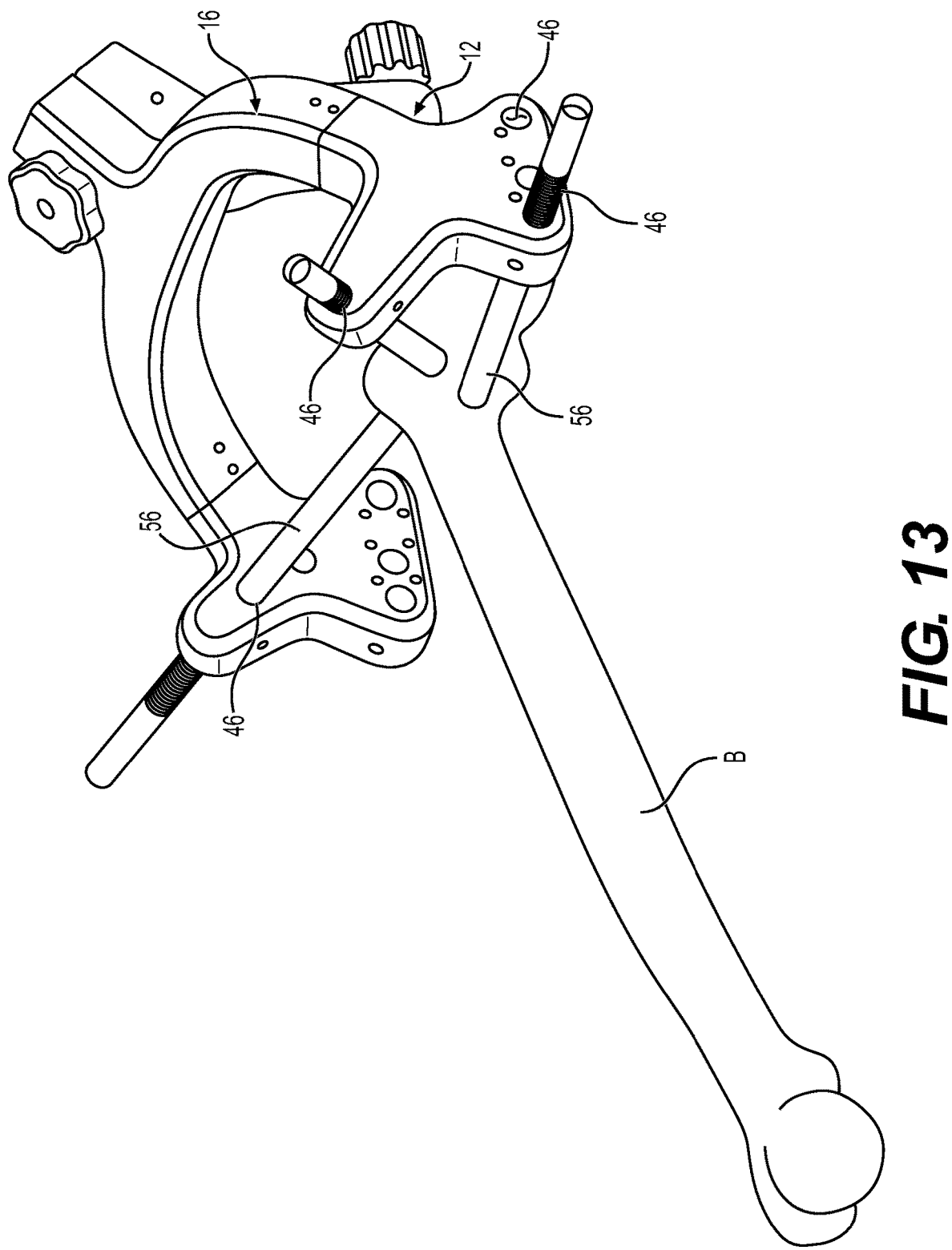
FIG. 13 is an alternative perspective views of the system shown in FIG. 6 including driver sleeves.
Figure 16:
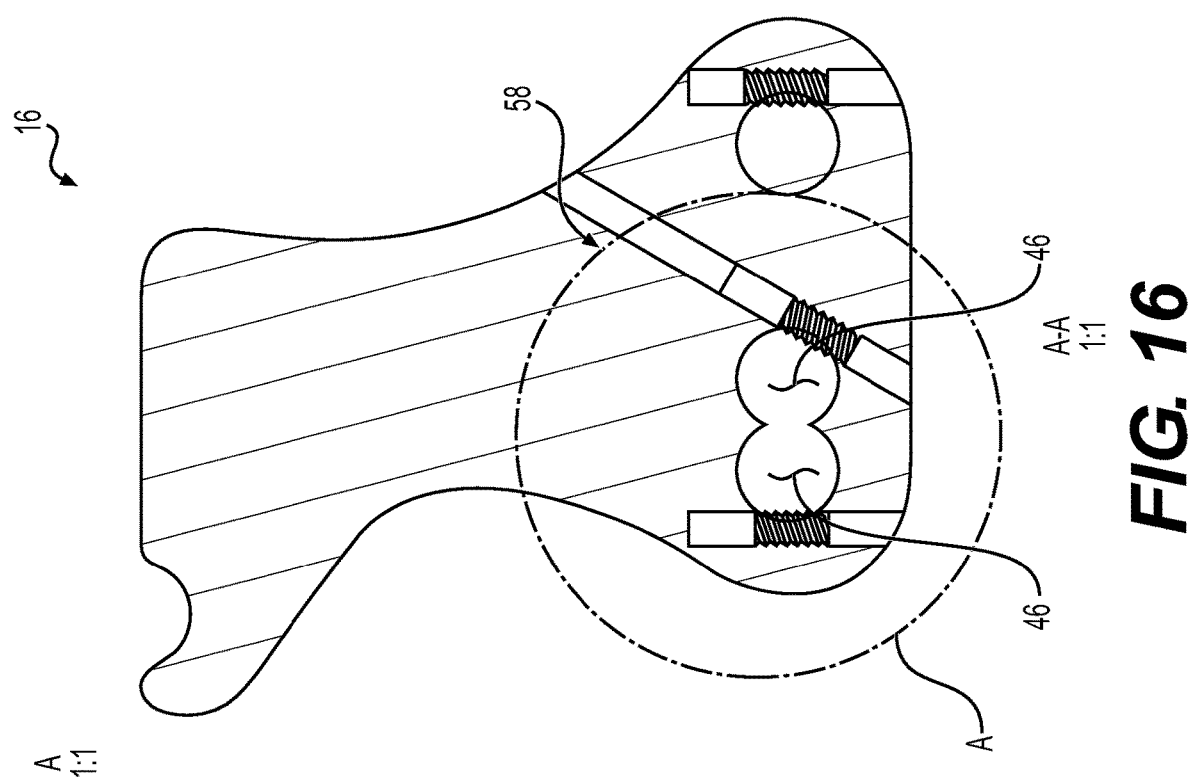
FIG. 16 is a cross-sectional view taken along line A-A in FIG. 15.
Figure 17:
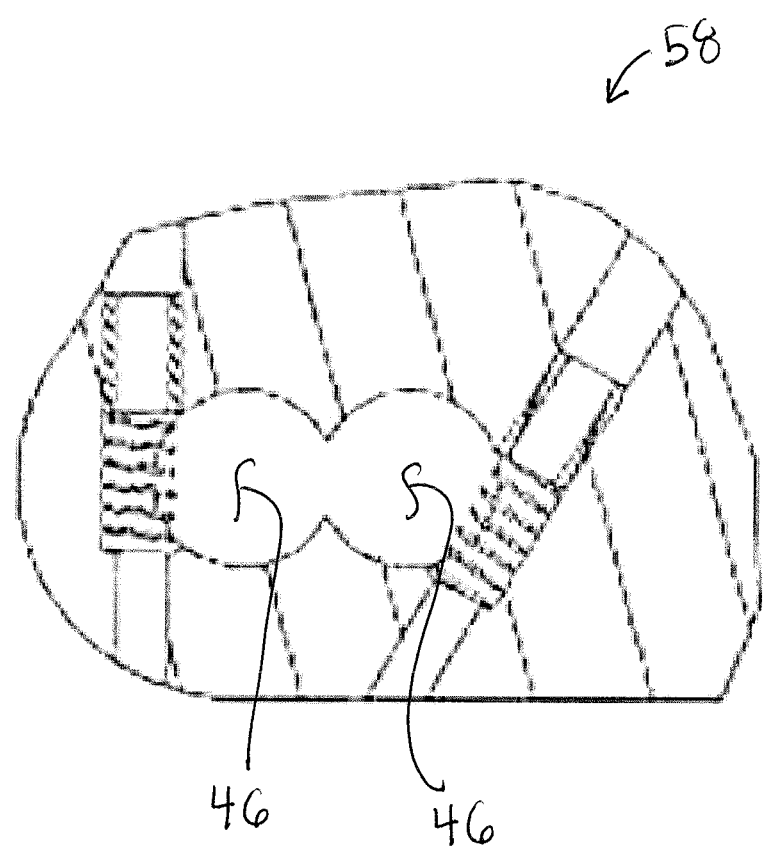
FIG. 17 is a detailed view of circle A in FIG. 16.

In some examples, as shown in FIGS. 9 and 13, one or more driver sleeves 56 may be extended through the targeting openings 46 for aligning and/or orienting the stabilizing fasteners. As shown in FIGS. 16 and 17, the aiming guide 16 may include or define one or more retention mechanisms 58 configured to retain one or more driver sleeves 56 in the targeting openings 46. The retention mechanism 58 may include, for example, a peak rod configured to control a movement of the driver sleeves 56. The peak rod may extend at least partially across the targeting opening 46 of the aiming guide 16 and may use deflection, due to material properties of the peak rod, to control movement of the one or more stabilizing fasteners. In some examples, the retention mechanism 58 of the aiming guide 16 includes a spring retention system that prevents a driver sleeve 56 from moving or falling out of the targeting openings 46. As shown in FIGS. 16 and 17, the spring retention system may include at least one spring configured to retain the driver sleeves 56. The springs may be retained in a pocket that is off center relative to the targeting opening 46 and may be configured to deflect when a driver sleeve 56 is inserted into the targeting openings 46 and exert a retaining force on an outer diameter of the driver sleeve 56 to prevent the driver sleeve 56 from falling out or slipping out of position. When the driver sleeve 56 is inserted into the targeting opening 46, the spring deflects and applies a retaining force to the outside of the driver sleeve 56 to prevent movement.

Figure 18:
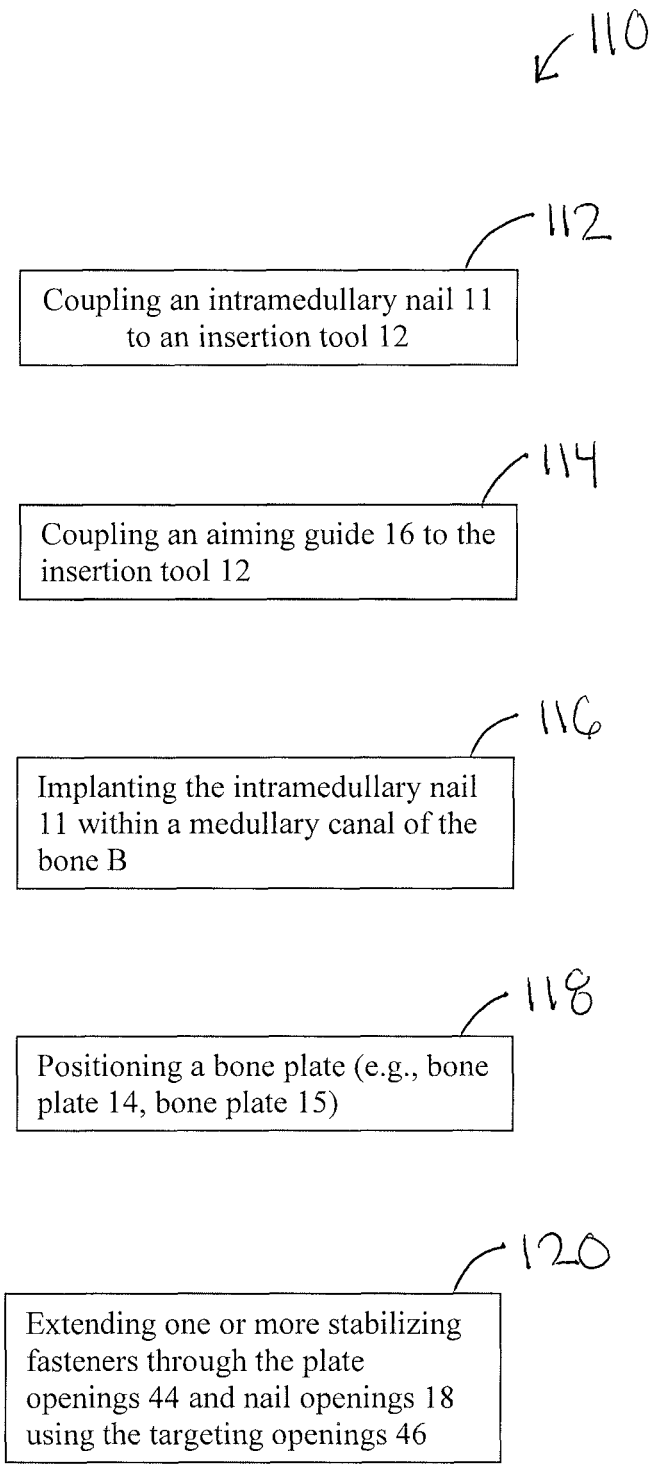
FIG. 18 is a flowchart of an example method for treating bone fractures.

Referring to FIG. 18, a method 110 for treating a fracture in a bone B includes coupling an intramedullary nail 11 to an insertion tool 12 at operation 112. The intramedullary nail 11 includes one or more nail openings 18 extending therethrough for receiving one or more stabilizing fasteners.

An aiming guide 16 is coupled to the insertion tool at operation 114. The aiming guide 16 includes one or more targeting openings 46 for receiving the stabilizing fasteners.

The intramedullary nail 11 is implanted within a medullary canal of the bone B at operation 116. With the aiming guide 16 coupled to the insertion tool 12, the aiming guide 16 is positioned and/or oriented such that the trajectory of one or more targeting openings 46 substantially matches or are coaxial with one or more nail openings 18 of the intramedullary nail 11.

A bone plate (e.g., bone plate 14, bone plate 15) is positioned at operation 118. The bone plate includes one or more plate openings 44 extending therethrough. The bone plate may be positioned such that the plate openings 44 are axially aligned with the targeting openings 46. By positioning the bone plate in this manner, the trajectory of the plate openings 44 substantially match or are coaxial with one or more nail openings 18.

One or more stabilizing fasteners are extended through the plate openings 44 and nail openings 18 using the targeting openings 46 at operation 120. The insertion tool 12 facilitates positioning the intramedullary nail 11 to aid in securing the bone B while the stabilizing fasteners are being guided into the plate openings 44 and/or nail openings 18. The stabilizing fasteners may be used to interlock the intramedullary nail 11 and bone plate to compress the condyle of the bone B. In this manner, at least some of the load may be distributed along the bone plate instead of being concentrated at the bone B and/or intramedullary nail 11, mitigating trauma to the bone and/or decreasing recovery time.

Examples described herein may be used to treat one or more bone fractures. When an insertion tool is coupled to an aiming guide, a user (e.g., a surgeon) may extend one or more stabilizing fasteners at least partially through an intramedullary nail implanted within a medullary canal of a bone with the naked eye (e.g., without fluoroscopy) by extending the stabilizing fasteners through the targeting openings of the aiming guide. In some examples, a bone plate may be positioned by aligning the plate openings of the bone plate with the targeting openings of the aiming guide. In this manner, the user may extend one or more stabilizing fasteners through the targeting openings of the aiming guide to extend the stabilizing fasteners through the plate openings of the bone plate and the nail openings of the intramedullary nail with the naked eye (e.g., without fluoroscopy).

When introducing elements of the present disclosure or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed:

1. A system for treating a fracture in a bone, the system comprising:
   an intramedullary nail including one or more nail openings extending therethrough for receiving one or more stabilizing fasteners, the intramedullary nail implantable within a medullary canal of the bone;
   a bone plate configured to engage an outer surface of the bone, the bone plate including one or more plate openings extending therethrough for receiving the one or more stabilizing fasteners, the one or more plate openings spaced about the bone plate such that the bone plate is positionable to axially align the one or more plate openings with the one or more nail openings when the intramedullary nail is implanted within the medullary canal of the bone;
   an aiming guide including one or more targeting openings for receiving the one or more stabilizing fasteners, the one or more targeting openings spaced about the aiming guide such that the aiming guide is positionable to axially align the one or more targeting openings with the one or more plate openings and the one or more nail openings for extending the one or more stabilizing fasteners therethrough when the intramedullary nail is implanted within the medullary canal of the bone; and
   an insertion tool coupleable to the intramedullary nail and the aiming guide, wherein the insertion tool includes a handle and the intramedullary nail couples to a lower portion of the handle and the aiming guide couples to an upper portion of the handle.

2. The system of claim 1, wherein the aiming guide is positioned such that the one or more targeting openings are axially aligned with the one or more nail openings when the insertion tool is coupled to the intramedullary nail and the aiming guide.

3. The system of claim 2, wherein the insertion tool includes an insertion shaft extending from the handle, the insertion shaft including one or more orientation tabs at a distal end thereof.

4. The system of claim 2, wherein the insertion tool includes an insertion shaft extending from the handle, the insertion shaft including one or more grooves defined in at a distal portion thereof.

5. The system of claim 2, wherein the insertion tool includes an insertion shaft extending at least partially through the handle, the insertion shaft including a flange at a proximal portion thereof seated in a groove defined in a proximal surface of the handle.

6. The system of claim 2, wherein the insertion tool includes an insertion shaft and a connection bolt, the connection bolt extending axially through the insertion shaft such that the connection bolt is axially translatable a predetermined distance.

7. The system of claim 2, wherein the insertion tool includes an insertion shaft and a connection bolt, the connection bolt extending axially through the insertion shaft, the insertion shaft including one or more internal threads, the connection bolt including one or more external threads configured to engage or cooperate with the one or more internal threads of the insertion shaft.

8. The system of claim 2, wherein the insertion tool includes an insertion shaft and a connection bolt, the connection bolt extending axially through the insertion shaft, the connection bolt including one or more external threads positionable in a cavity defined by the insertion shaft.

9. The system of claim 2, wherein the insertion tool includes an insertion shaft and an assembly shaft extending axially through the insertion shaft such that a distal end of the assembly shaft extends beyond a distal end of the insertion shaft.

10. The system of claim 2, wherein the insertion tool includes a connection bolt defining an undercut groove and an assembly shaft including a latching feature that interfaces with the undercut groove in the connection bolt.

11. The system of claim 2, wherein the insertion tool includes a connection bolt including one or more internal threads, and a backslap shaft including one or more external threads configured to engage the one or more internal threads.

12. The system of claim 2, wherein the aiming guide includes one or more locating pins and the insertion tool includes one or more locating pin openings defined therein for receiving the one or more locating pins.

13. The system of claim 2, wherein the aiming guide includes a threaded knob and the insertion tool includes a threaded insert defined therein for receiving the threaded knob.

14. The system of claim 1, wherein the aiming guide has a wishbone-shaped configuration including a first leg and a second leg, a first targeting opening of the one or more targeting openings extending through the first leg, a second targeting opening of the one or more targeting openings extending through the second leg.

15. The system of claim 1, wherein the aiming guide includes one or more retention mechanisms configured to control a movement of one or more driver sleeves extended through the one or more targeting openings.

* * * * *